United States Patent [19]
Smith et al.

[11] Patent Number: 5,562,882
[45] Date of Patent: Oct. 8, 1996

[54] STERILE LIQUID BARRIER TRANSFER COUPLING

[75] Inventors: David T. Smith, West Sussex; Julian J. Wilkins, Norfolk, both of United Kingdom; Heidi J. Studebaker, Indianapolis, Ind.

[73] Assignees: Eli Lily and Company, Indianapolis, Ind.; Total Process Containment Limited, Surrey, United Kingdom

[21] Appl. No.: 355,959

[22] Filed: Dec. 14, 1994

[30] Foreign Application Priority Data

Dec. 15, 1993 [GB] United Kingdom ............... 9325667

[51] Int. Cl.⁶ ........................................................ A61L 2/06
[52] U.S. Cl. ........................... 422/26; 422/295; 422/297; 422/300
[58] Field of Search .................. 422/26, 292, 295, 422/297, 300; 141/90, 91

[56] References Cited

U.S. PATENT DOCUMENTS 4,242,310  12/1980  Greff et al. ..................... 422/300
5,397,547   3/1995  Woolhouse et al. ............. 422/26

OTHER PUBLICATIONS

Sales literature entitled, "Connection Without Breaking the Containment", la Calhène, publication date unknown.

*Primary Examiner*—Robert Warden
*Assistant Examiner*—Theresa T. Snider
*Attorney, Agent, or Firm*—Schwegman, Lundberg, Woessner & Kluth

[57] ABSTRACT

A flexible tube is sterilized and ready for coupling to sterile tubing in a sterile environment by steam sterilization in a closed environment in which steam pressure both inside and outside the flexible tube is the same. For this purpose, the flexible tube is coupled to a transfer cup which has door means sealingly attached at its mouth creating a chamber, which is openable when the coupling is to take place. An outlet from the transfer cup chamber thus defined allows sterilizing steam entering said chamber from the flexible tube with the door means in closed disposition to leave the transfer cup therethrough and flow around the exterior of the flexible tube at the same pressure as the steam within the tube. Once the flexible tube and transfer cup are sterilized, the flexible tube is coupled to the sterile tubing by admission of said tubing to the transfer cup chamber through the door means.

12 Claims, 10 Drawing Sheets

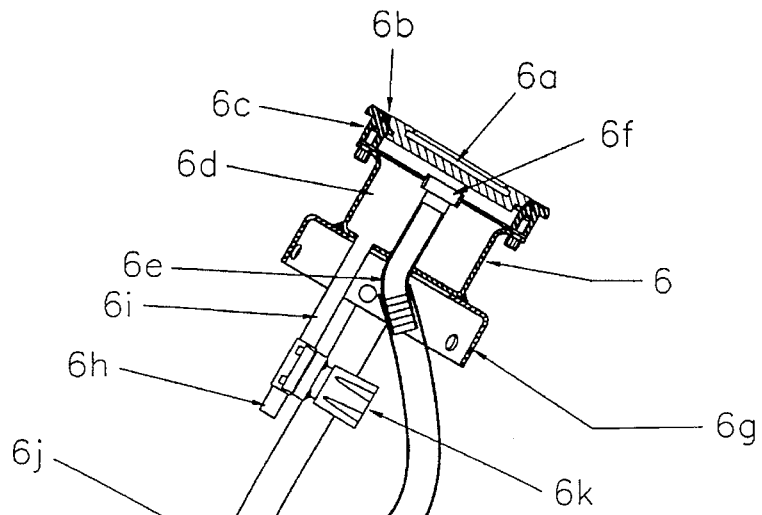
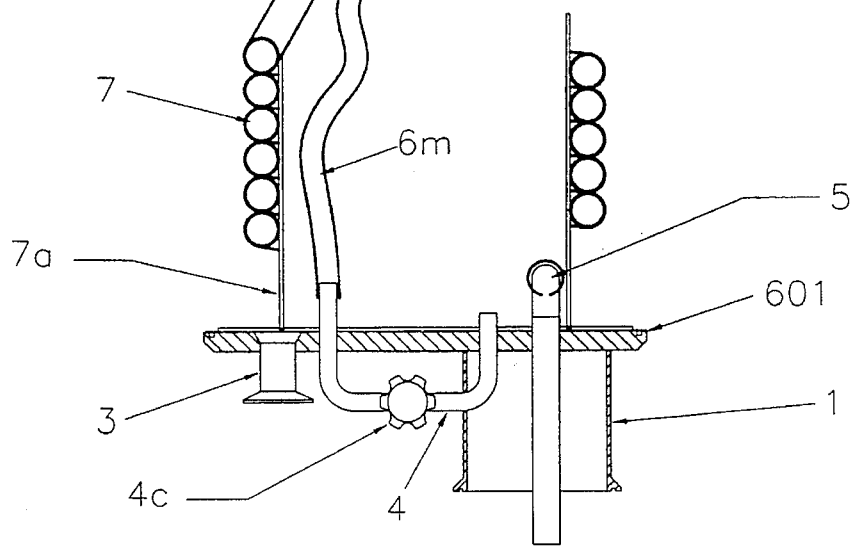
FIG. 3
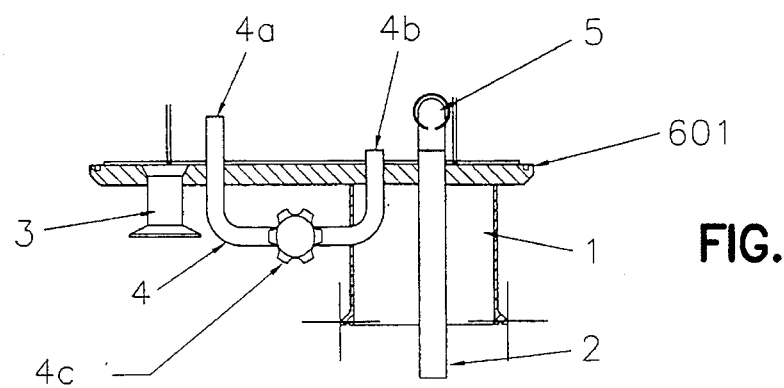
FIG. 2

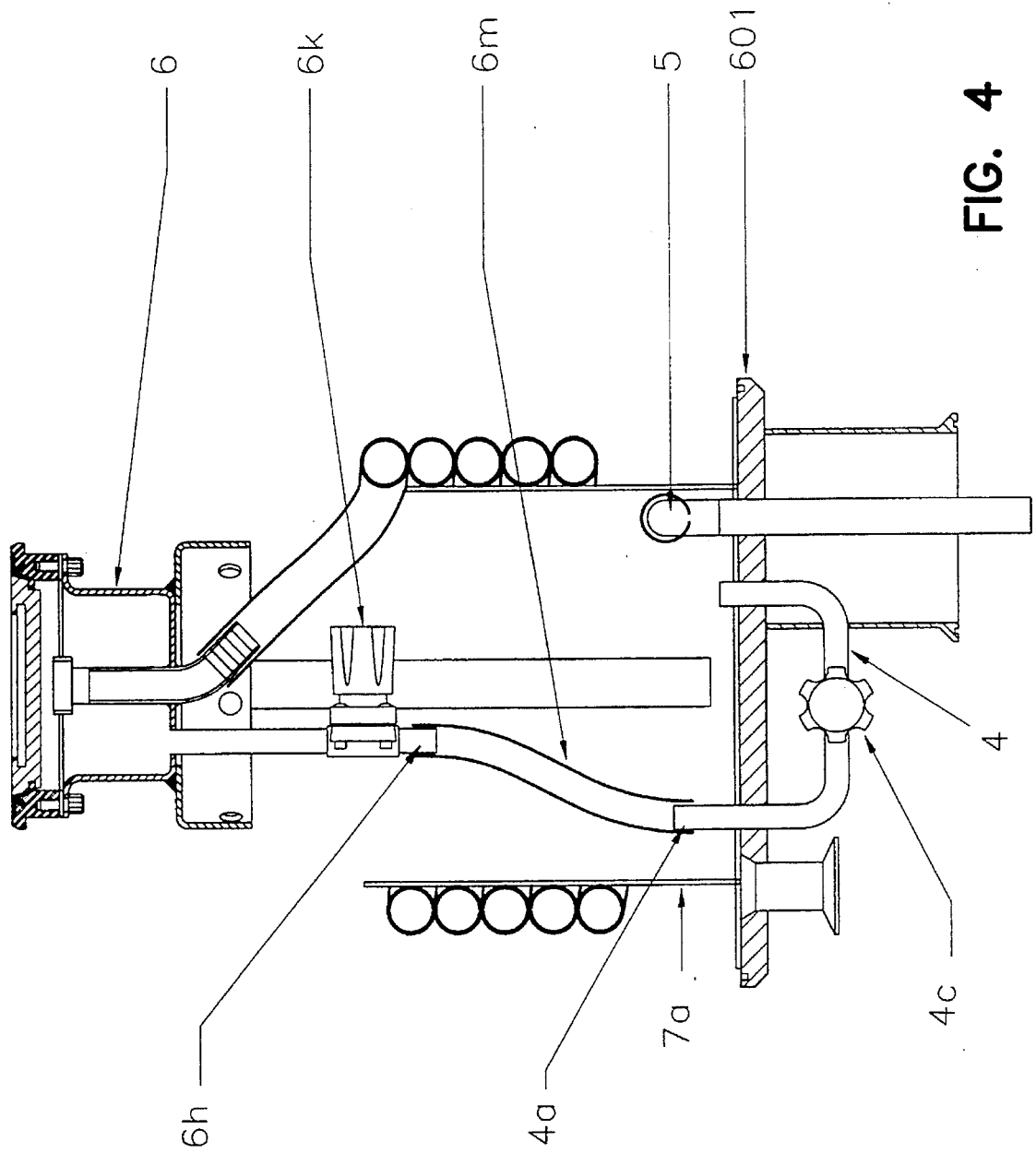

5,562,882

STERILE LIQUID BARRIER TRANSFER COUPLING

BACKGROUND OF THE INVENTION

This invention relates to the sterilization of liquid barrier transfer couplings for use in the pharmaceutical manufacturing industry.

Many pharmaceutical manufacturing facilities develop from small scale operation. Nevertheless the manufacturing standards, controls and protocols imposed by, for example, the Medical Control Agency in the United Kingdom and the Federal Drug Administration in the United States, are of necessity the same whatever the size of facility. These are established around such general needs as that for the aseptic particulate and microbiological conditions to be maintained in the zone immediately surrounding a product whenever the product will otherwise be exposed to the environment. There is a need for absolute barrier technology and automatic systems to be used to minimize human interventions in processing areas thereby to produce significant advantages in assurance of sterility of manufactured products.

The economics of manufacture have influenced how closed solution manufacturing vessels may be installed in a relatively low grade environmental area. Manufactured solutions are pumped through barriers such as sterile area walls or containment isolators to vial filling machines. The interconnecting pipework between vessel and filling machine and also recirculation pipework are normally permanently installed continuous stainless steel pipes to enable steam sterilisation to be carried out. The pipework is designed to self-drain and is rated to withstand the operating pressure and to meet statutory requirements for pressure testing.

Efficient utilisation of the plant has resulted in a demand for a number of processing vessels to feed more than one filling machine. The consequent provisions for switching over of pipe connections are complex to engineer, requiring pipe manifolds and considerable numbers of valves. Silicone piping linked as required from a nominated process vessel to a designated vial filling machine offers an attractive measure of cost reduction, flexibility of operation and general weight reduction. It is readily cleaned and may be sterilised. However, the piping must subsequently be connected aseptically both to a filling machine and to a process vessel. The connection techniques currently available are frequently not acceptable in not meeting standards imposed by control agencies or even for general reasons of quality assurance.

A particular way in which such flexible silicone piping might be employed would be for it to be used for transferring a manufacturing batch to a filling apparatus after which it would be subjected to in situ washing and sterilization. Steam sterilization in an autoclave would be the recommended approach but such piping is not pressure rated and, as such, cannot be steam sterilized using conventional pressurised steam sterilizing technology.

SUMMARY OF THE INVENTION

It is an object of the present invention to provide a method and apparatus for steam sterilizing relatively thin walled piping, particularly in such manner as to be applicable to flexible piping attached to a coupling system which allows for coupling of the piping to, for example, a filling system to take place in sterile manner.

According to one aspect of this invention, there is provided a method of steam sterilizing the interior of a flexible tube which comprises the steps of providing a flexible tube having two open ends;

providing a transfer cup having a mouth, door means associated with the mouth of the cup and capable of travel between an open position and a closed position wherein the mouth is sealingly closed to define within the transfer cup a chamber, inlet means to the chamber and outlet means from the chamber to be utilized with the said door closed;

connecting one end of the flexible tube to said inlet means;

positioning the transfer cup with transfer tube connected to its inlet means and said door means closed in a vessel and sealing said vessel closed with said outlet from the transfer cup communicating said chamber with the interior of the sealed vessel;

supplying steam to the interior of said flexible tube at the flexible tubes other end for a predetermined time, whereby the steam passes through the flexible tube and the transfer cup to issue therefrom at said outlet means and flow around the exterior of the tube within the sealed vessel under the same pressure as that at which it is supplied to the tube;

terminating supply of the steam to the interior of said flexible tube;

closing the outlet means; and opening said vessel and removing therefrom the flexible tube with transfer cup attached and both their interiors sterile.

According to a second aspect of the invention, there is provided an assemblage for forming an apparatus for utilization in the steam sterilization of the interior of a flexible tube, the assemblage comprising a transfer cup having a mouth, door means associated with said mouth and capable of travel between an open position and a closed position at which the mouth is sealingly closed to define within the transfer cup a chamber, inlet means to the transfer cup adapted to receive one end of a flexible tube to enable steam travelling through the flexible tube to issue into the transfer cup and outlet means form the transfer cup having a closure valve;

a vessel having wall means provided in fluid tight manner with entry means for steam connectable to the other end of said flexible tube, steam removal means, a wall aperture sized to allow through passage of the transfer cup into the vessel and closure means associated with the wall aperture for closing thereof in fluid tight manner;

in which apparatus, the outlet means from the transfer cup is positioned for steam to issue therefrom into the interior of said vessel to flow around the exterior of said flexible tube under the same pressure as that at which it is supplied to the flexible tube before removal of the steam through the steam removal means.

It is particularly preferred for the transfer cup to form part of a high containment transfer cup assembly comprising a pressure tight passive door set in a passive frame to be docked with a complementary pressure tight active door set in an active frame with appropriate sealing measures being adopted to ensure that there can be no ingress of contamination between the doors when coupled together, both while in their respective frames and when displaced therefrom to provide a through opening. A suitable form of door arrangement for such purpose is described in GB-A-2262786.

A tube to be sterilized will generally be attached to a connector tube which extends through the base of the transfer cup and which at its end remote from the base is provided with a pipe coupling for attachment, when the door opening is present, to a pipe leading to, for example, a vial filling arrangement within a sterile room.

The method of the invention will generally be carried out within an autoclave having a bottom wall to be covered by a bell jar shaped cover and through which appropriate piping passes. Thus, through the bottom wall of the autoclave will pass an inlet tube from a source of sterilizing steam or sterile medium to be filled into vials as the case may be, and an outlet tube for spent sterilizing steam and optionally the opposed limbs of a U-bend, one limb of which is connectable by means of suitable small bore tubing with the outlet from the transfer cup and the other of which opens into the interior of the autoclave for admission thereinto of sterilizing steam to circulate around the exterior of the flexible tube which is preferably formed of silicone rubber, so as to sterilize the exterior thereof as well as the interior thereof before the sterilizing steam condensing in the lower part of the autoclave leaves through the outlet therefrom.

BRIEF DESCRIPTION OF THE DRAWINGS

For a better understanding of the invention, and to show how the same may be carried into effect, reference will now be made, by way of example only, to the accompanying drawings, wherein:

FIG. 2 is a section through the base part of a bell jar assembly according to FIG. 1 modified according to use in accordance with the present invention;

FIG. 3 shows the elements to be within the bell jar assembly at the time of steam sterilization;

FIG. 4 shows the orientation of the transfer vessel contents when within the bell jar assembly immediately prior to steam sterilization;

DETAILED DESCRIPTION OF THE PREFERRED EMBODIMENT

Figure 1:
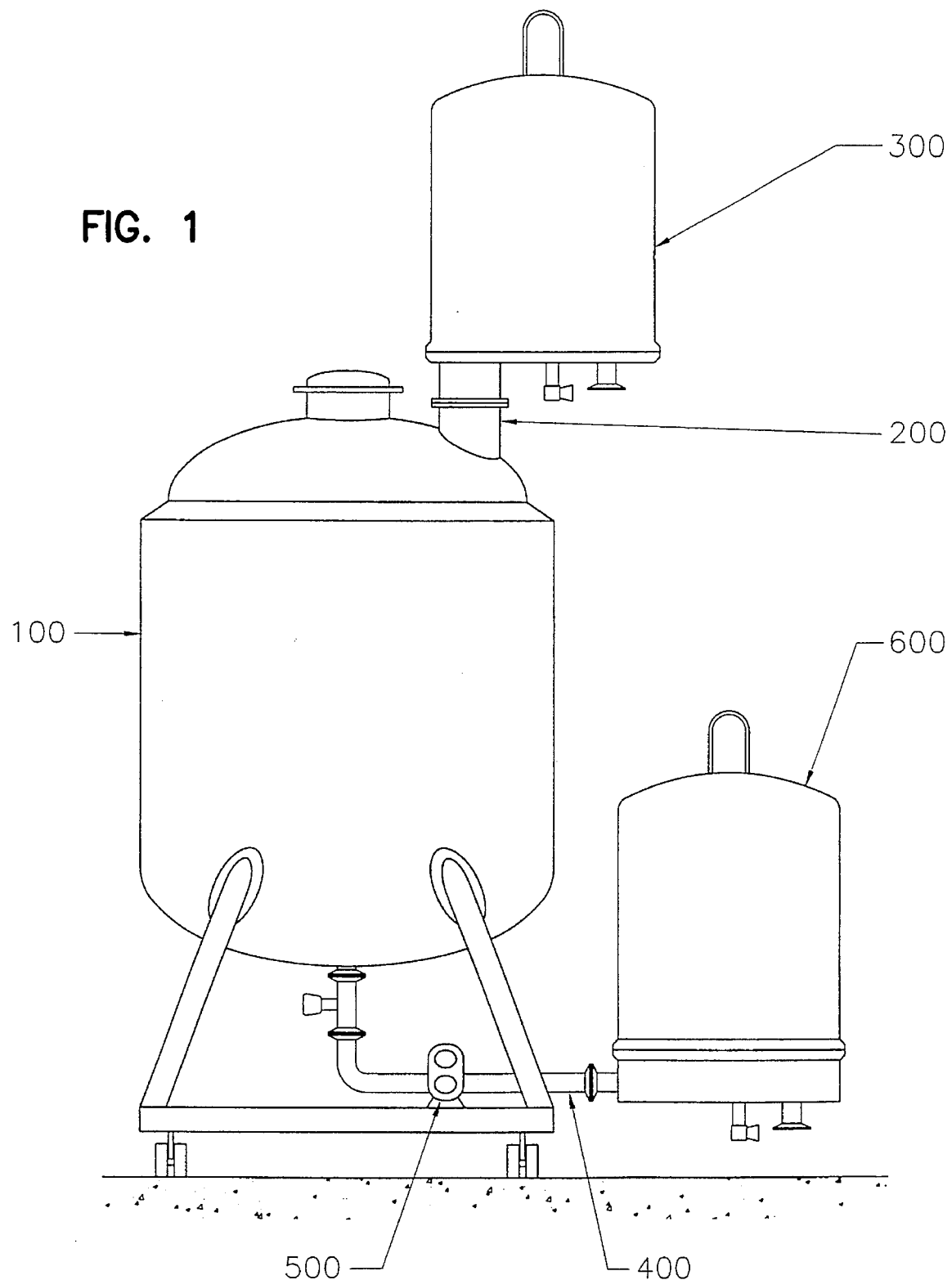
FIG. 1 shows in elevation a liquid transport vessel with associated bell jar assemblies.

Referring firstly to FIG. 1, there is shown a mobile vessel 100 connected via piping 200 at its upper end with an inlet bell jar assembly 300 and which is connected at its lower end through piping 400 via peristaltic pump 500 with an outlet bell jar assembly 600. Both inlet bell jar assembly and outlet bell jar assembly have a similar role in housing flexible ducting through which the mobile vessel is to be connected sterilely to process equipment. In the case of inlet bell jar assembly 300, its ducting is connected to manufacturing plant and in the case of outlet bell jar assembly 600, its ducting is to be connected to vial filling equipment. Depending on requirements there may be more than one inlet bell jar assembly and/or more than one outlet bell jar assembly attached to the mobile vessel. Similar sterile requirements are placed upon the flexible ducting passing through both inlet and outlet bell jar assemblies and for convenience the sterilization thereof will be described specifically with reference to outlet bell jar assembly 600.

Thus referring to FIG. 2, there is shown the base 601 of a bell jar assembly of the type typically required for suspensions where recirculation of fluid is to take place through vessel and pipe flue to prevent settling and to maintain consistent solution concentration. The bell jar assembly is pressure rated to match the pressure specification of mobile vessel 100 such that both vessel and bell jar assembly can be steam sterilized in situ. The base 601 sits on a flanged stool 1 inside which is a nozzle 2 passing through the base 601 and terminating in a barbed ferrule 5. Spaced apart from the flange stool 1 at another opening in the base 601 is a flanged nozzle 3 for connection to a condensate trap and drain. Passing through two additional openings in the base 601 are the limbs of a U-bend 4, free ends of which are to be located within the bell jar and one of which is a barbed ferrule 4a and the other a simple stub end 4b. The U-bend 4 is equipped with a valve 4c intermediate its ends.

As shown in FIG. 3, a silicone tube 7 to be sterilised is coiled around a mandrel 7a, the silicone rubber tube 7 being connected at one end to ferrule 5 and at the other end to a high containment transfer cup assembly 6 which itself comprises a pressure tight passive door 6a, seal 6b and passive frame 6c bolted to a chamber-defining steam cup 6d and whose functioning will be described in greater detail later. The steam cup houses a barbed nozzle 6e which is connected to the silicone tube 7 and which projects into the cup to terminate in a sanitary pipe coupling 6f. A location cup 6g is welded back-to-back with the steam cup 6d and has a specific role when docking of the transfer cup assembly 6 at a wall plate arrangement takes place, as will be described hereinafter. An outlet tube 6i with barbed nozzle 6h passes from the steam cup 6d through the location cup 6g and is fitted with a valve 6k. Extending into the location cup 6g from below is a long handle 6j whose use will be described later. A small bore silicone hose link 6m is shown attached to barbed ferrule 4a of U-bend 4. Initially, the equipment shown in FIG. 3 will not be sterile. The assembly and operation of the system will now be described with reference to FIGS. 4 to 6.

Figure 5:
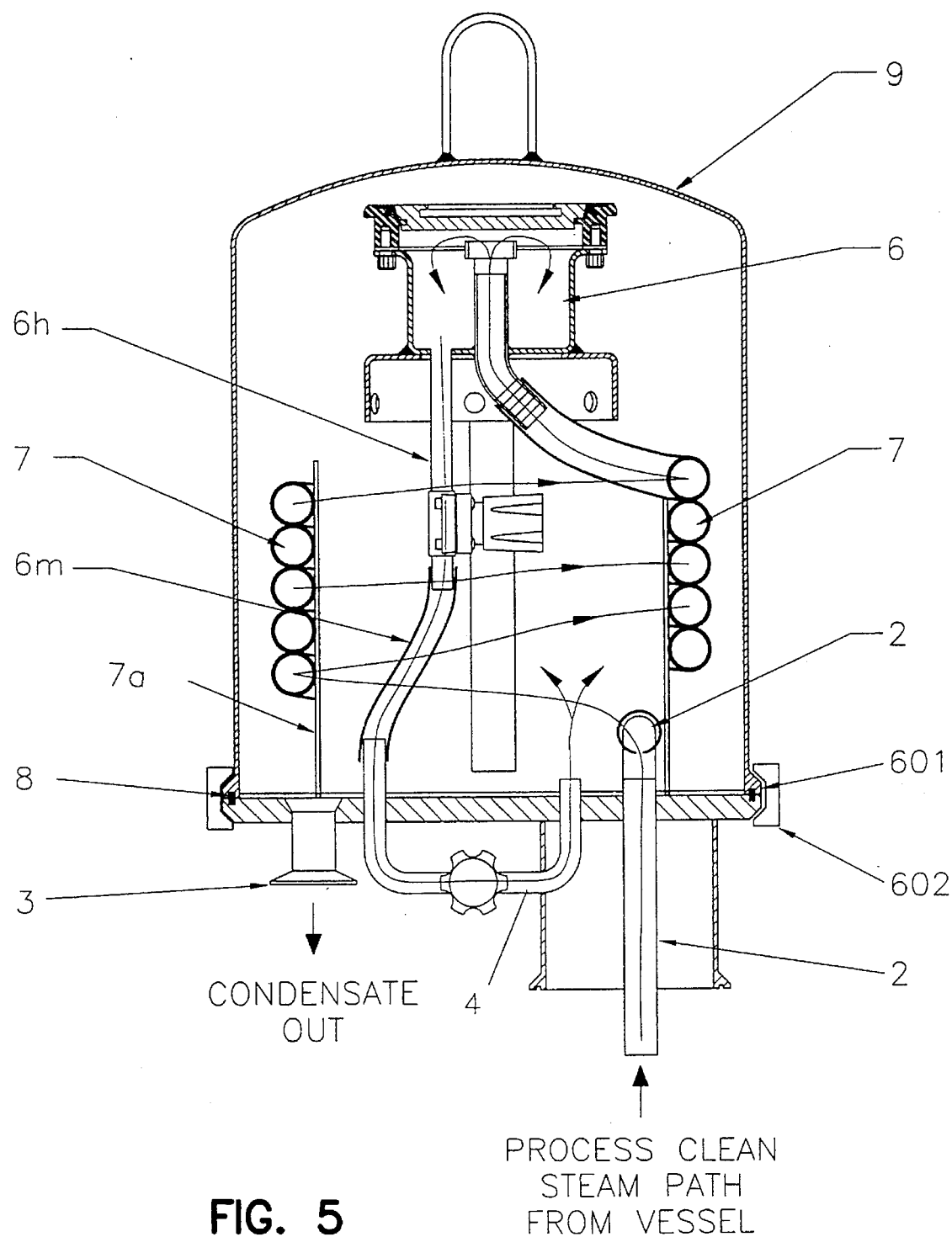
FIG. 5 is a like view to FIG. 4 showing the assembled bell jar assembly at the time of steam sterilization flow of steam therethrough as during steam sterilization.

Initially valves 4c and 6k are opened and mandrel 7a is placed on the bell jar base 601. Flexible tube 7 is connected to the barbed ferrule 5 and is wound around the mandrel 7a which is to act as its support. The free end of flexible tube 7 (the upper end) is connected to the transfer cup valve nozzle 6e. To achieve the arrangement shown in FIG. 4, the transfer cup assembly 6 is lowered onto location brackets (not shown) carried by the mandrel 7a. At this stage, the short length of small bore flexible hose 6m which is shown already connected to U-bend 4 in FIG. 3 is also connected to barbed nozzle 6h. A bell jar gasket 8 is placed in a channel in the bell jar base 601 and a bell jar cover 9 is lowered into place. A quick release clamp bracket 602 is used to connect and seal the bell jar base 601 and bell jar cover 9. (FIG. 5). The apparatus is now ready for carrying out steam sterilization of the flexible silicone tube within the bell jar housing 9 in the manner shown in FIG. 5. A supply (not shown) of clean steam under pressure, say 1 atmosphere gauge, to mobile vessel 100 is opened. As a result, the steam travels through pipe 400 to enter the bell jar through nozzle 2 to travel through the helically wrapped flexible tube 7. The cleaning steam then flashes off into the steam cup 6d and passes out from this through tube 6i, tube link 6m finally to percolate through U-bend 4 to enter the free interior of bell jar housing 9. The condensing steam leaves via nozzle 3 to a steam trap (not shown) through which the condensed steam is drained off. After a validated steam temperature/time cycle, sterilization of the bell jar and its tubing contents, both internally and externally, is complete. As a result of the same steam pressure obtaining within and outside the silicone tubing, there are no problems of pressure damage to the silicone tubing.

Figure 6:
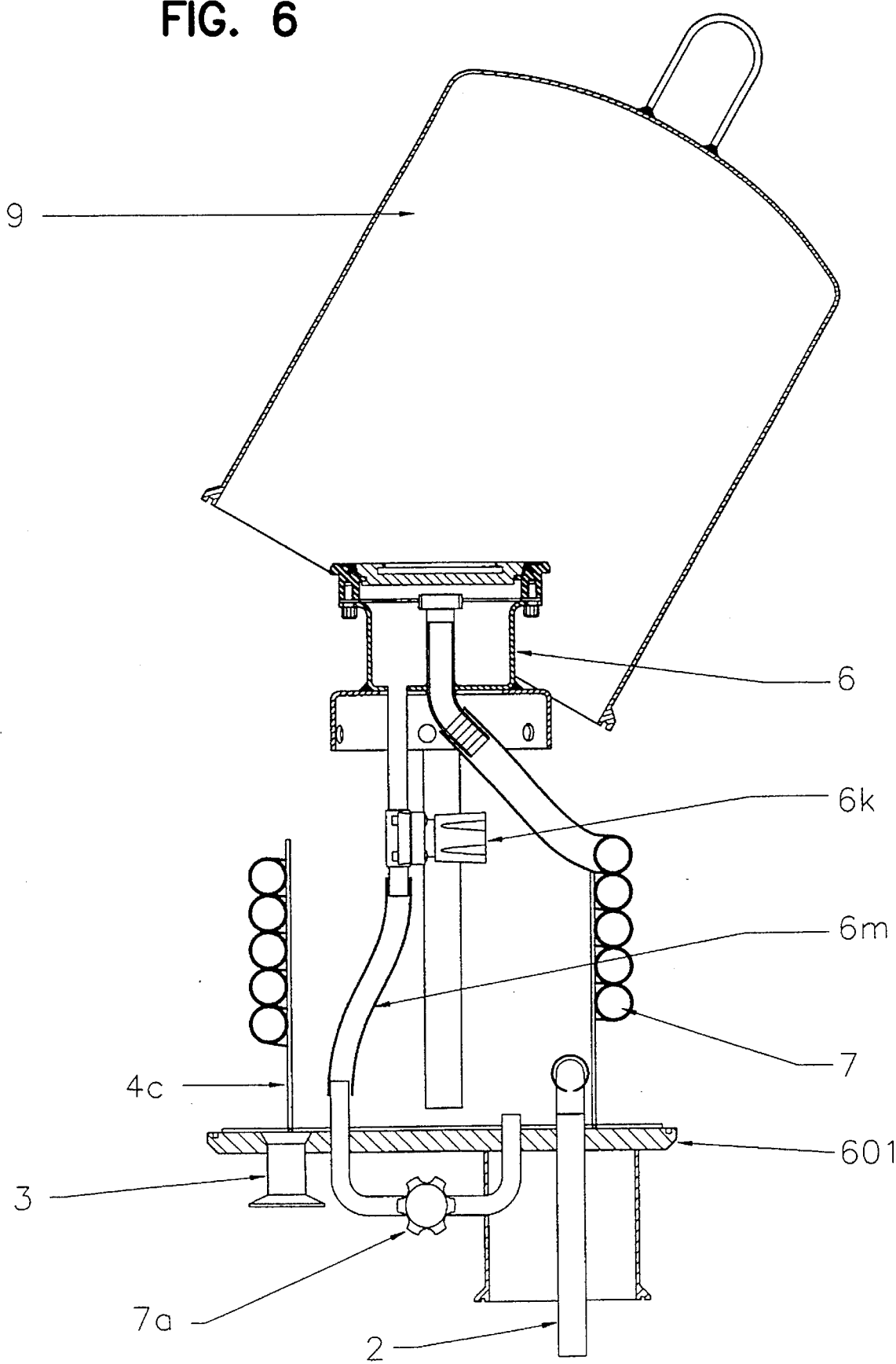
FIG. 6 is a like view to FIG. 5 showing the bell jar assembly cover in the process of its disassembly.

At this stage it is important that it is the interior of the tubing which has been sterilized. Valve 4c is now closed to isolate the internal volume of the bell jar 9 from the interior of the flexible tube 7 and transfer cup 6. The bell jar housing 9 is released from the base 1 and is then removed therefrom (FIG. 6). Finally, valve 6k which is now accessible is closed and tube link 6m is uncoupled from tube 6i. The disposition of the various elements is now the same as in FIG. 3, but the entire closed system is sterile and out of contact with the ambient atmosphere and the exterior of tube 7 and the interior of vessel 100 have been steam cleaned. At this stage the transfer cup assembly 6 is withdrawn from the location brackets of the mandrel 7a and the flexible tube 7 is unwound from the mandrel.

Figure 7:
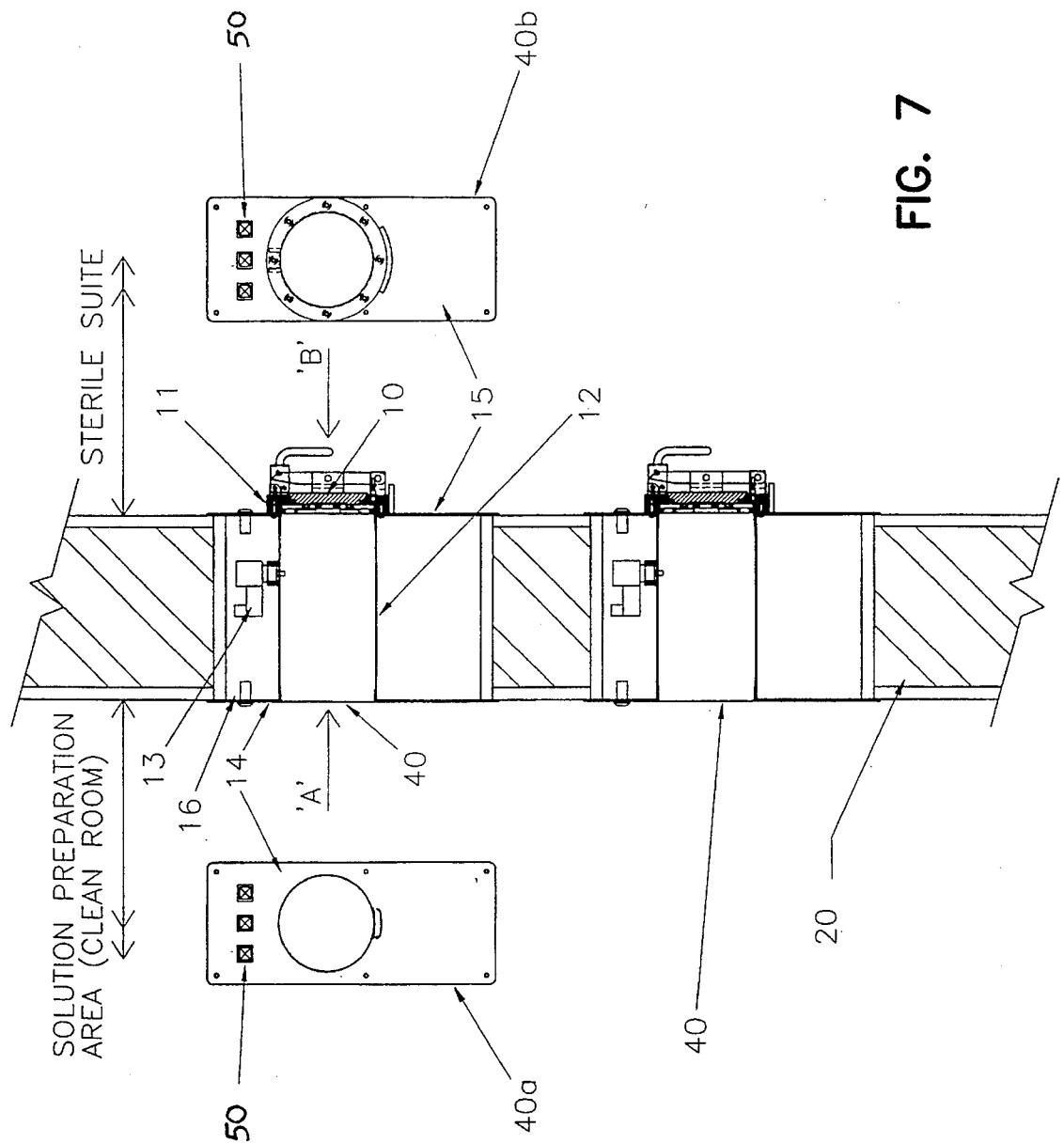
FIG. 7 is a section through a wall plate arrangement at which coupling is to take place.

FIG. 7 of the accompanying drawings shows a section through a masonry wall 20 in which there are located one above the other a pair of wall plate connectors 40. Plan views of the wall plate connectors from within a solution preparation area, i.e. clean room and from within a vial filling area i.e. sterile suite are shown as details 40a and 40b respectively. Each wall plate connector comprises a door 10 mounted within a frame 11 located on the sterile suite side at one end of a barrier guide tube 12 which is open at the other end. Barrier guide tube 12 is effectively set between a pair of plates 14 and 15 on the clean room and sterile suite sides respectively and defines an annular chamber 16 in the upper part of which is located a solenoid bolt 13. Wall plates 14 and 15, besides sealing the barrier tube 12 into the wall, also house door indicator lights 50.

Figure 8:
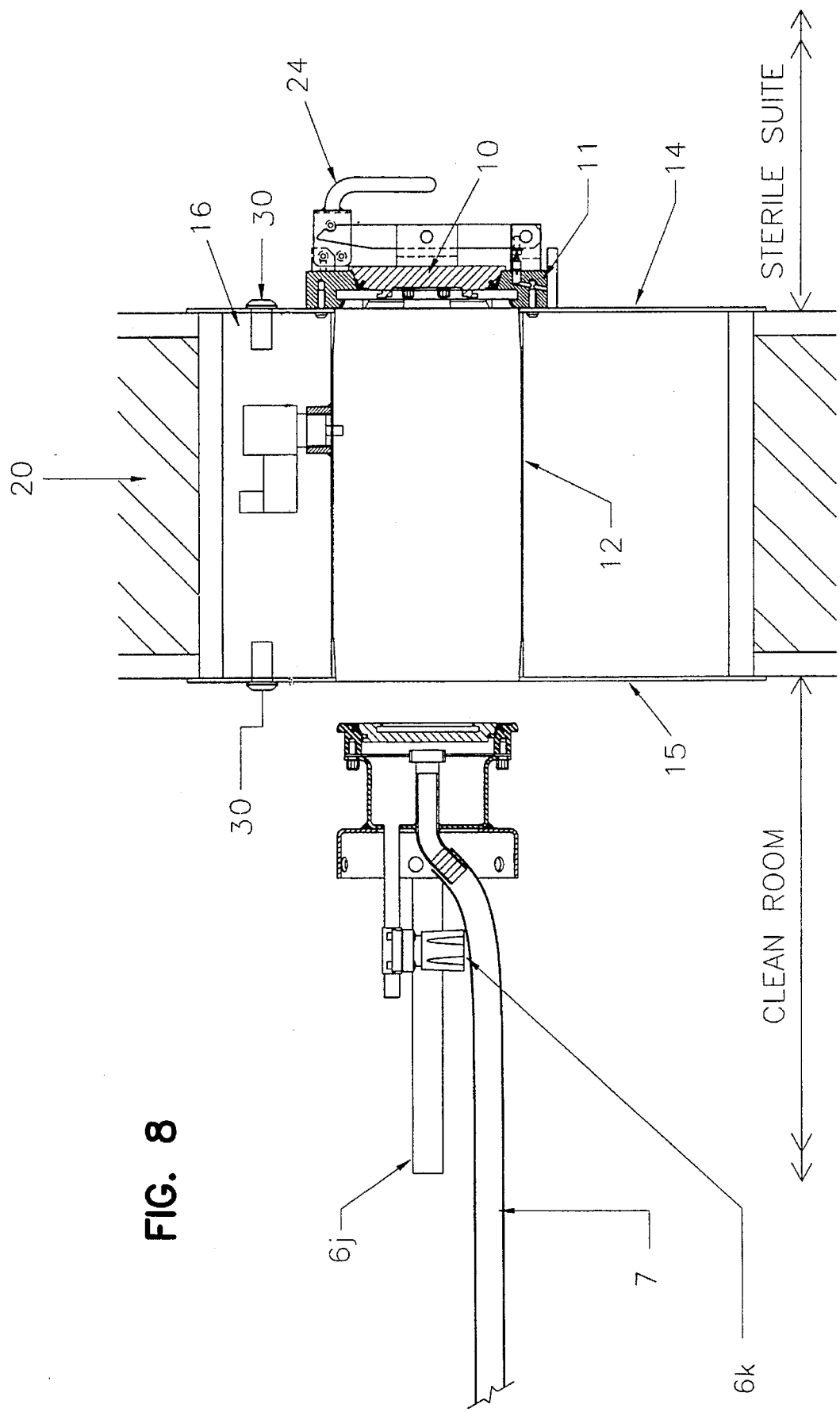
FIG. 8 shows the contents of the aforementioned bell jar assembly immediately prior to docking at the wall plate.
Figure 9:
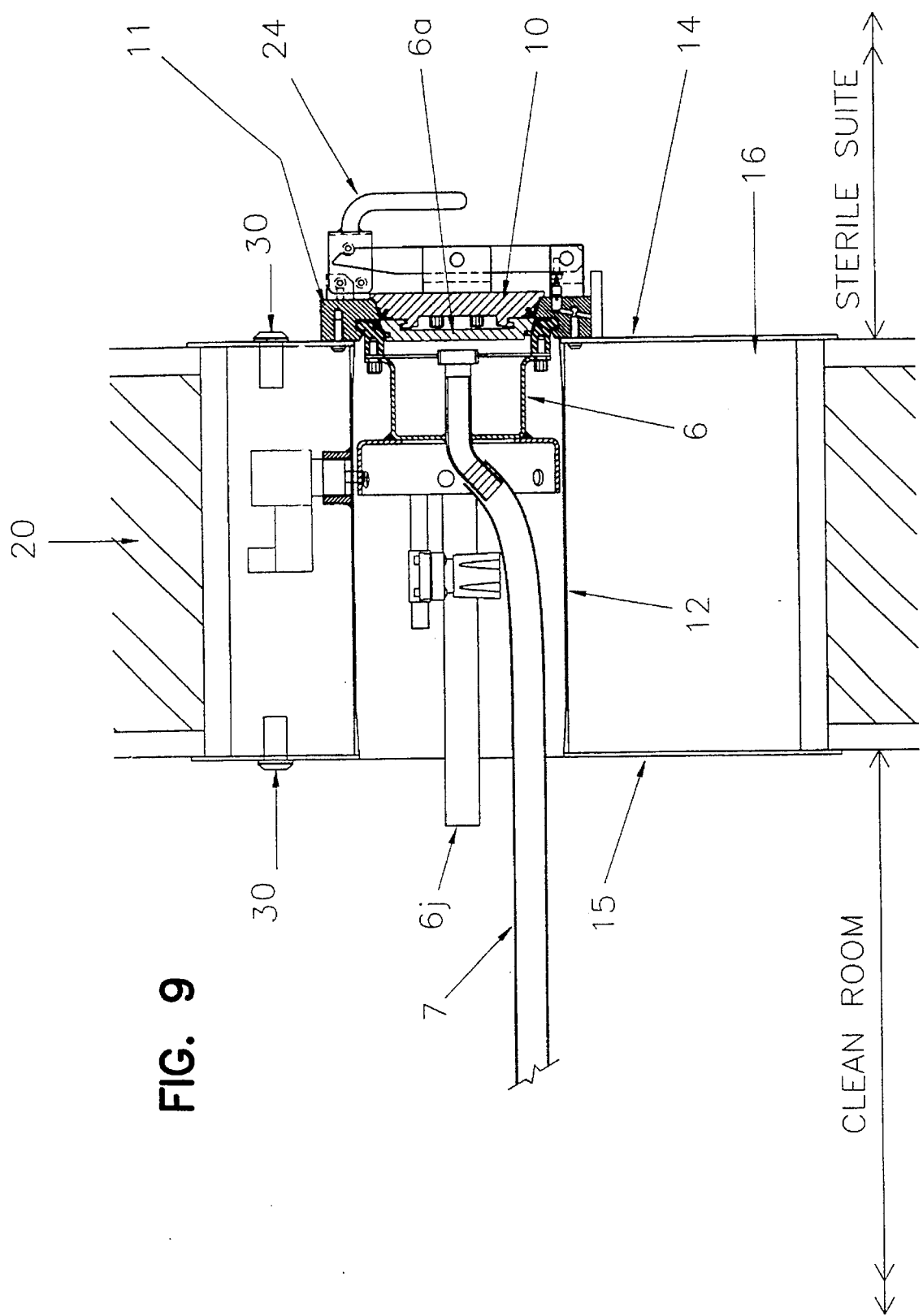
FIG. 9 shows the arrangement of FIG. 8 when docking of the bell jar assembly at the wall plate has taken place.

Referring next to FIG. 8, the first step in the utilization of the barrier device of FIG. 7 is shown. High containment transfer cup assembly 6 whose interior is in a sterile state and carrying flexible tube 7 which is internally sterile is offered to the barrier guide tube 12. It is pushed therethrough by means of handle 6j and docking thereof at the active frame 11 and provision of communication between tube 7 and the interior of the sterile suite are achieved by rotation of handle 6j about its longitudinal axis.

Figure 12:
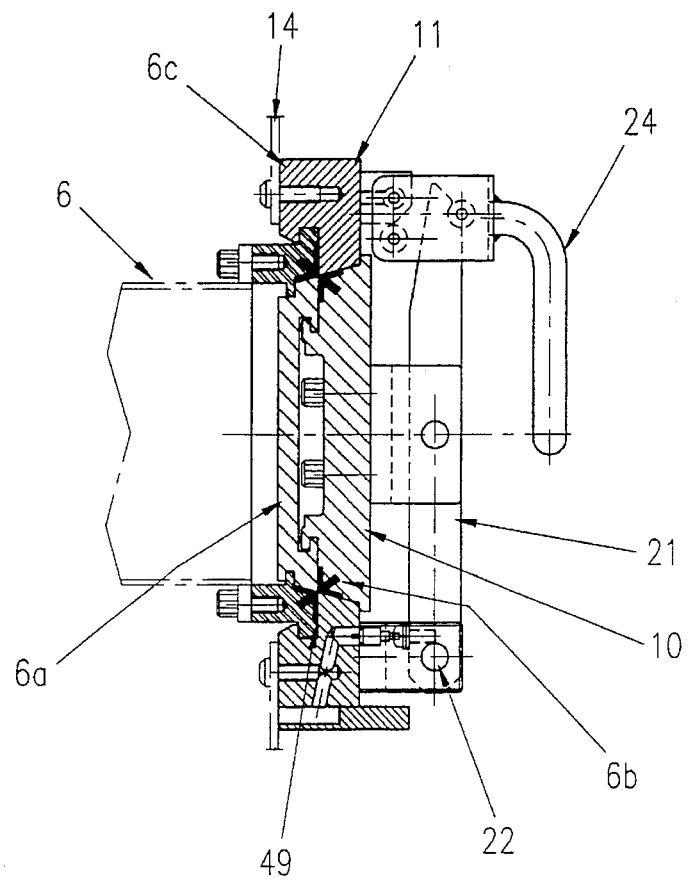
FIG. 12 is a like-sectional view to that shown in FIG. 11 showing the respective components when docking has taken place.
Figure 11:
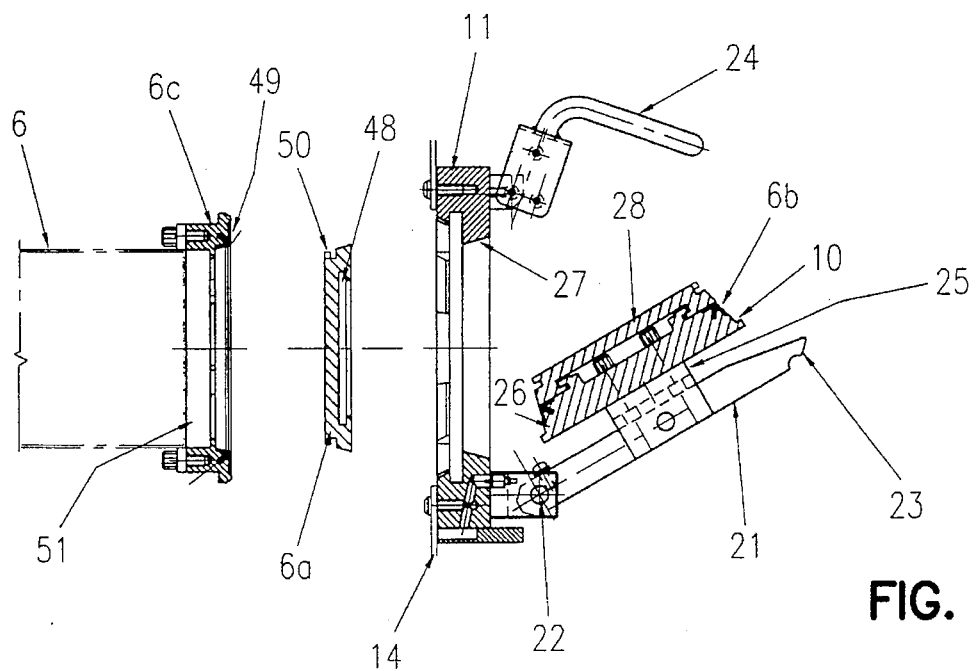
FIG. 11 is an exploded view in section of the components of the rotary docking fitting for coupling the contents of the cup assembly to a port.

In FIGS. 11 and 12 frame 11 can be seen to carry at a hinge 22 a bar 21 formed at its distal end with a clasp 23 engageable by a latch assembly 24 mounted on the frame 11 opposite the hinge 22. The bar 21 carries a bracket 25 to which is attached the door 10 which is a male fitting. The male door has a peripheral surface, shown here at 26, which is conical, reducing in diameter towards its forward end and matching a like shaped internal surface 27 of the frame 11. At its front surface, the door is provided with a plurality of holding cams 28 arranged around a circle at intervals, as mate members, and able to enter arcuate channels 48, as female members, in a door 6a belonging to a docking unit of assembly 6. This enables the doors to engage/disengage through appropriate rotation of the transfer vessel relative to the storage unit. An intimate engagement between doors is achieved and ingress of material between door to contaminate their external surfaces is prevented by corner seals 6b and 49 carried by the respective doors.

Frame 6c secured around the mouth of the transfer cup assembly provides a conically narrowing opening in which door 6a rotationally engages through holding cams 50 spaced at intervals in circular formation on door 6a able to enter arcuate channels 51 in frame 6c. In general, herein, it is of course arbitrary which element of a pair of associated elements has holding cams and which has arcuate grooves, provided that coupling and uncoupling of elements can take place as required.

FIG. 12 shows the two frames 6c and 11 coupled, with door 6a and door 10 engaged but with the combined doors in a closed position awaiting unlatching of the hinged bar 21 to allow passage of material into the sterile suite from tube 7.

Having now described the fixing and displaceable portions of the door arrangement, the actions necessary to transfer material from tube 7 into the sterile suite will now be described. Engagement is first effected between the frames of the transfer cup assembly wall plate connector, male/female location of the frames with respect to each other takes place and through rotation of the transfer cup assembly through a predetermined angle by means of handle 6j engages the frames. At the same time there will have been male/female location of the doors to one within the other and a further rotation of the sample transfer vessel with respect to the host unit engages the doors. If each rotation amounted to 15°, there will have been a total rotation of 30°. The male doors will, at the same time have been disengaged from the female frames in which one of the doors was previously held by holding cam/channel engagement, i.e. door 10 and door 6a are no longer locked in arcuate channels 48 and 28 respectively. The hinge bar clasp is now unlatched, opened and the doors which form a physical barrier between the tube 7 and the sterile area are displaced allowing direct access from the interior of one to the interior of the other. Manipulation of the latch is effected remotely by the operator.

Figure 10:
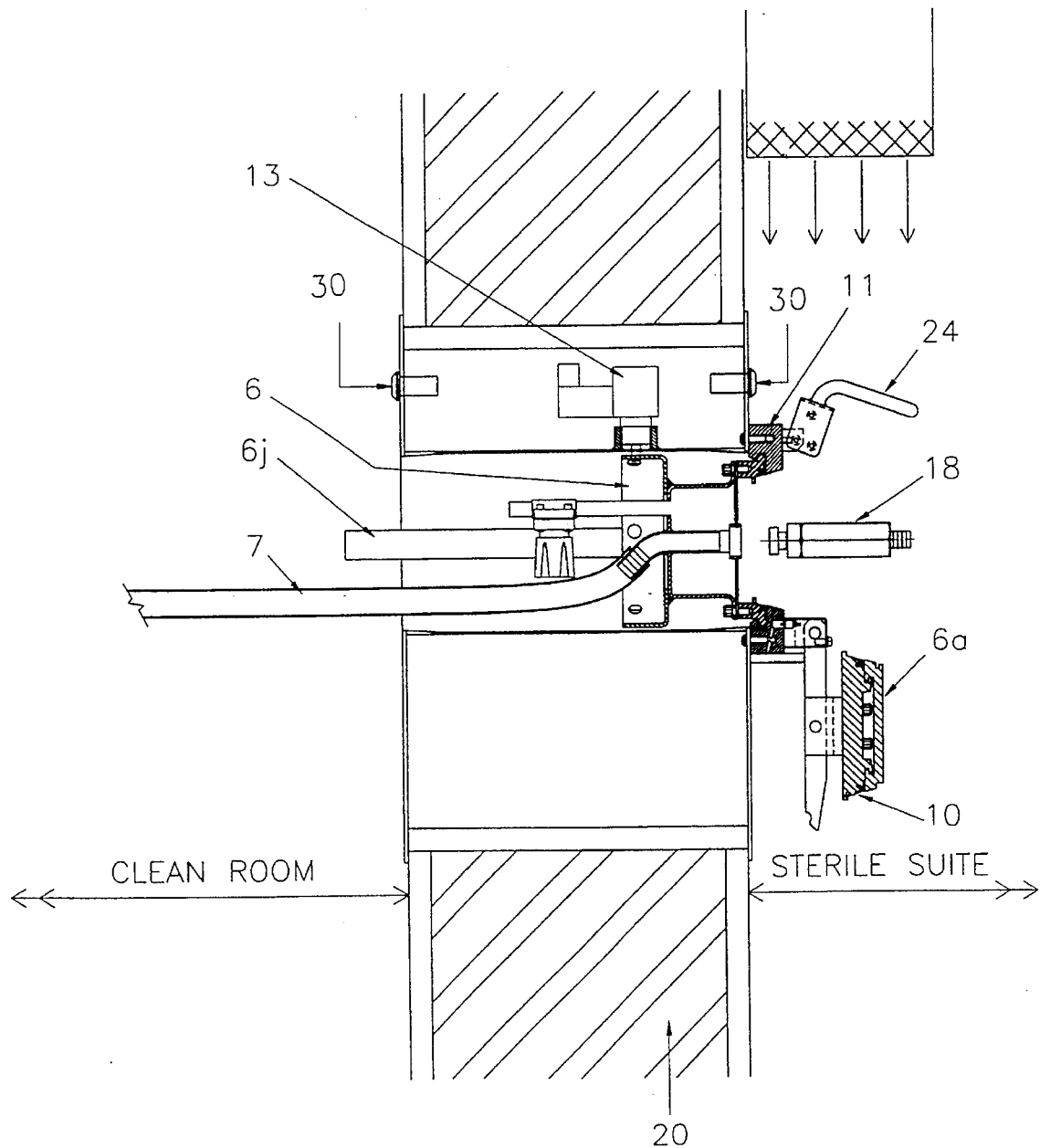
FIG. 10 shows an incoming tube about to be coupled to a further tube leading to vial filling apparatus.

FIG. 10 shows the doors engaged at which time the solenoid bolt 13 will be in alignment with the locking device on location cup 6g. Indicator lights 30 will then indicate that it is safe to remove the cup on the clean side and that it is safe to open the door on the sterile side. When latch 24 of the door 10 is released and the coupled combination of the door 6a and door 10 is hinged open from the frame 11 into the interior of the sterile room, the action of hinging the doors open activates the solenoid bolt 13 to lock the transfer cup assembly 6 onto the active frame.

At this stage the sterile tube 7 is exposed for connection to the interior of the sterile room and while subjecting the area around the hinged open doors 6a and 10 to a laminar air flow from a hood 17, a sanitary union of sterile tubing 18 to a filler arrangement (not shown) with pipe coupling 6f, which at this stage is located in the opening produced by hinging back the doors 6a and 10, is made. The apparatus is now ready for supply of sterile solution to vials in the interior of the sterile suite for use in filling valves. The indicator lights should indicate that the cup should not be removed on the clean side while on the sterile side it is safe to open the door.

We claim:

1. A method of steam sterilizing the interior of a flexible tube which comprises the steps of providing a flexible tube having two open ends;

providing a transfer cup having a mouth, door means associated with the mouth and capable of travel between an open position and a closed position wherein the mouth is sealingly closed to define within the transfer cup a chamber, inlet means to the chamber and outlet means from the chamber to be utilized with the said door closed;

connecting one end of the flexible tube to said inlet means;

positioning the transfer cup, with flexible tube connected to its inlet means and said door means closed, in a vessel and sealing said vessel closed with said outlet means from the transfer cup communicating said chamber with the interior of the sealed vessel;

supplying steam to the interior of said flexible tube at the flexible tube's other end for a predetermined time, whereby the steam passes through the flexible tube and the transfer cup to issue therefrom at said outlet means and flow around the exterior of the tube within the sealed vessel under the same pressure as that at which it is supplied to the tube;

terminating supply of the steam to the interior of said flexible tube;

closing the outlet means; and opening said vessel and removing therefrom the flexible tube with transfer cup attached and both their interiors sterile.

2. A method as claimed in claim 1, wherein said flexible tube is formed of silicone rubber.

3. A method as claimed in claim 1 or 2, comprising the additional steps of winding a section of said flexible tube around a mandrel, placing the mandrel with flexible tube wound thereon within the sealed vessel and keeping the flexible tube section wound around the mandrel as steam is passed through the interior of the flexible tube.

4. A method as claimed in claim 1 or 2, wherein said sealed vessel has wall means, first and second openings in said wall means and duct means passing sealingly out of the sealed vessel through the first said opening and extending by way of a section positioned externally of the vessel, where the duct means is equipped with a valve, to re-enter the vessel through the second said opening in the wall means, the method comprising the additional steps of coupling one end of the duct means to the outlet means from the transfer cup chamber prior to the passage of steam through the flexible tube, of closing said valve on termination of passage of steam through the flexible tube and then, when said outlet means has been closed, uncoupling the duct means form the outlet means.

5. A method as claimed in claim 1 or 2 wherein, during the course of the sterilizing, steam which has issued into the interior of the sealed vessel passes out therefrom via an outlet to a condensate trap as a mixture of steam and water.

6. A method of providing an internally sterile combination of a flexible tube whose interior is initially not sterile and sterile tubing located within a sterile environment and ready for the transfer of a sterile fluid from the flexible tube to the sterile tubing, comprising the steps of sterilizing the interior of the flexible tube according to the method in any one of the preceding claims to provide said flexible tube with transfer cup attached and their interiors sterile; providing door means to a sterile environment in which said sterile tube is located, the door means being couplable to the door means of the transfer cup; coupling the respective door means to one another; displacing the coupled door means to provide communication between the interior of the transfer cup and the sterile environment and bringing together and coupling the flexible tube and the sterile tubing.

7. A method as claimed in claim 6, wherein one said door means is provided with a plurality of holding cams arranged around a circle at intervals as male members and the other door means is provided with matching arcuate channels as female members, in which method the door means are opposed to one another and rotated one with respect to the other to effect coupling of the respective door means as the holding cams enter the arcuate channels.

8. An assemblage for forming an apparatus for utilization in the steam sterilization of the interior of a flexible tube, the assemblage comprising a transfer cup having a mouth, door means associated with said mouth and capable of travel between an open position and a closed position at which the mouth is sealingly closed to define within the transfer cup a chamber, inlet means to the transfer cup case constructed to receive one end of a flexible tube to enable steam travelling through the flexible tube to issue into the transfer cup and outlet means from the transfer cup having a closure valve;

a vessel having wall means provided in fluid tight manner with entry means for steam connectable to the other end of said flexible tube, steam removal means, a wall aperture sized to allow through passage of the transfer cup into the vessel and closure means associated with the wall aperture for closing thereof in fluid tight manner;

in which apparatus, the outlet means from the transfer cup is positioned for steam to issue therefrom into the interior of said vessel to flow around the exterior of said flexible tube under the same pressure as that at which it is supplied to the flexible tube before removal of the stem through the steam removal means.

9. An assemblage as claimed in claim 8, wherein said fluid tight closure means for said aperture is a base member therefor and an entry duct for steam extends through said base member.

10. An assemblage as claimed in claim 9, wherein said base member is formed additionally with first and second openings, a duct means passes through both said openings to provide a duct section external to the vessel when the latter is closed by the base member, valve means is provided in said duct section and one end of the duct has associated means for coupling thereof to the outlet means from the transfer cup.

11. An assemblage as claimed in claim 9 or 10, wherein said base member has a third opening therethrough for steam which has flowed around the exterior of the flexible tube to issue through to leave said vessel, the assemblage additionally comprising a condensate trap and drain for connection to said third opening.

12. An assemblage as claimed in claims 9 or 10, wherein the base member carries a mandrel for winding of said flexible tube therearound.

\* \* \* \* \*

UNITED STATES PATENT AND TRADEMARK OFFICE
CERTIFICATE OF CORRECTION

PATENT NO. : 5,562,882

DATED : October 8, 1996

INVENTOR(S) : Smith et al.

It is certified that error appears in the above-identified patent and that said Letters Patent is hereby corrected as shown below:

On Column 2, line 16, delete "tubes" and insert --tube's --therefor.

On Column 5, line 62, delete "mate" and insert --male --therefor.

Signed and Sealed this

Twenty-ninth Day of July, 1997

Attest:

BRUCE LEHMAN

Attesting Officer

Commissioner of Patents and Trademarks